(12) United States Patent
Nardone et al.

(10) Patent No.: US 8,585,723 B2
(45) Date of Patent: Nov. 19, 2013

(54) COIL ANCHOR SYSTEMS AND METHODS OF USE

(75) Inventors: Christopher Nardone, N. Chelmsford, MA (US); Marcia Buiser, Marlborough, MA (US)

(73) Assignee: Boston Scientifc Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/336,973

(22) Filed: Dec. 23, 2011

(65) Prior Publication Data

US 2012/0095501 A1    Apr. 19, 2012

Related U.S. Application Data

(62) Division of application No. 12/246,817, filed on Oct. 7, 2008, now abandoned.

(60) Provisional application No. 60/979,965, filed on Oct. 15, 2007.

(51) Int. Cl.
*A61B 17/08* (2006.01)
*A61M 29/00* (2006.01)

(52) U.S. Cl.
USPC .......................................... 606/158; 606/200

(58) Field of Classification Search
USPC ................. 606/193, 194, 195, 200, 157, 158;
623/1.16, 1.12, 1.21, 1.22, 1.15, 23.72,
623/1.11
See application file for complete search history.

(56) References Cited

U.S. PATENT DOCUMENTS

| | | | |
|---|---|---|---|
| 4,994,069 | A | 2/1991 | Ritchart et al. |
| 5,226,911 | A | 7/1993 | Chee et al. |
| 5,522,822 | A | 6/1996 | Phelps et al. |
| 5,549,624 | A | 8/1996 | Mirigian et al. |
| 5,700,258 | A | 12/1997 | Mirigian et al. |
| 5,733,329 | A | 3/1998 | Wallace et al. |
| 5,916,235 | A | 6/1999 | Guglielmi |
| 6,024,765 | A | 2/2000 | Wallace et al. |
| 6,168,622 | B1 | 1/2001 | Mazzocchi |
| 6,361,558 | B1 | 3/2002 | Hieshima et al. |
| 6,569,179 | B2 | 5/2003 | Teoh et al. |
| 6,569,190 | B2 | 5/2003 | Whalen, II et al. |
| 6,635,068 | B1 | 10/2003 | Dubrul et al. |
| 6,660,020 | B2 | 12/2003 | Wallace et al. |
| 6,663,607 | B2 | 12/2003 | Slaikeu et al. |
| 6,682,546 | B2 | 1/2004 | Amplatz |
| 6,706,055 | B2 | 3/2004 | Douk et al. |
| 6,802,851 | B2 | 10/2004 | Jones et al. |

(Continued)

FOREIGN PATENT DOCUMENTS

| | | |
|---|---|---|
| WO | WO 2001/03607 A2 | 1/2001 |
| WO | WO 2007/006139 A1 | 1/2007 |
| WO | WO 2007041131 A1 | 4/2007 |

*Primary Examiner* — Dianne Dornbusch
(74) *Attorney, Agent, or Firm* — Bingham McCutchen LLP

(57) ABSTRACT

Vessel occlusion method including the steps of positioning a coil anchor in a large diameter blood vessel, wherein the coil anchor includes a radially expandable sidewall, a proximal opening dimensioned to receive an embolic coil, a distal opening, and the coil anchor further comprising at least one coil retaining element configured to retain an embolic coil within the blood vessel. The vessel occlusion method further including the steps of expanding the coil anchor within the blood vessel; and delivering at least one embolic coil into the blood vessel, wherein the retaining element prevents the at least one embolic coil from migrating downstream of the coil anchor.

9 Claims, 6 Drawing Sheets

(56) References Cited

U.S. PATENT DOCUMENTS

| | | |
|---|---|---|
| 6,866,677 B2 | 3/2005 | Douk et al. |
| 6,881,217 B2 | 4/2005 | Israel |
| 6,936,055 B1 | 8/2005 | Ken et al. |
| 6,984,240 B1 | 1/2006 | Ken et al. |
| RE38,972 E | 2/2006 | Purdy |
| 7,011,677 B2 | 3/2006 | Wallace et al. |
| 7,048,752 B2 | 5/2006 | Mazzocchi et al. |
| 2002/0161395 A1 | 10/2002 | Douk et al. |
| 2003/0093111 A1 | 5/2003 | Ken et al. |
| 2003/0149475 A1 | 8/2003 | Hyodoh et al. |
| 2003/0208256 A1 | 11/2003 | DiMatteo et al. |
| 2004/0193246 A1* | 9/2004 | Ferrera .................. 623/1.15 |
| 2005/0033349 A1* | 2/2005 | Jones et al. .................. 606/200 |
| 2005/0267570 A1 | 12/2005 | Shadduck |
| 2006/0009798 A1 | 1/2006 | Callister et al. |
| 2006/0009799 A1 | 1/2006 | Kleshinski et al. |
| 2006/0036263 A1 | 2/2006 | Stinson |
| 2006/0085028 A1 | 4/2006 | Boock |
| 2006/0095071 A1 | 5/2006 | Zhang |

* cited by examiner

COIL ANCHOR SYSTEMS AND METHODS OF USE

RELATED APPLICATION DATA

The present application is a divisional of copending U.S. patent application Ser. No. 12/246,817, filed Oct. 7, 2008, which claims the benefit of U.S. provisional application Ser. No. 60/979,965, filed Oct. 15, 2007, and the contents of which are incorporated herein by reference in their entirety.

TECHNICAL FIELD

The present invention relates to the field of vascular devices and, more particularly, to systems and methods for anchoring embolic coils.

BACKGROUND

Various medical conditions call for partial or complete occlusion of blood vessels or vascular formations. Aneurysms can be treated by filling a defect with embolic coils, polymers, or other materials to promote thrombus formation and relieve vessel wall pressure. Similarly, cardiac septal defects may be treated with occlusion devices configured to expand to fill the defect and block unwanted blood flow. Also, cancer can be treated using occlusion devices to restrict blood supply to tumors.

Embolic coils have proven popular for vessel occlusion owing to the ability to place such coils in aneurysms and other vascular formations using percutaneous techniques. Improved deployment technology has permitted enhanced positioning of embolic coils using readily available imaging systems, such as fluoroscopy. In addition, the occlusive effectiveness of embolic coils has been furthered by incorporating thrombosis-promoting fibers in the coil structure, and by adopting space-filling coil conformations.

While embolic coils have undergone significant development, there remains room for further improvements. Currently, the use of embolic coils in large diameter blood vessels is limited due to the risk of coil migration caused by higher blood flow. Unlike coils delivered into a recessed anatomical feature (e.g., an aneurysm), embolic coils placed in high-flow blood vessels risk being swept downstream of a target location, and potentially lodging at other locations. Such unwanted coil movement can lead to incomplete vessel occlusion at the target location and necessitate additional procedures to remove a migrated coil.

The coil anchor system of the present disclosure solves one or more of the problems set forth above.

SUMMARY

Described herein are various methods and systems for preventing unwanted migration of an implantable device, particularly, embolic coils. In one embodiment, a coil anchor is disclosed for implanting within a vascular structure, such as, for example, a blood vessel. Once implanted, an inner portion of the implanted coil anchor can receive and trap embolic coils. The trapped coils can then initiate occlusion of the blood vessel at the desired location without the risk of coil migration.

In a first aspect, the coil anchor includes an anchor body configured for placement within a large diameter and/or high flow blood vessel, wherein the anchor body includes a radially expandable sidewall, a proximal opening dimensioned to receive an embolic coil, and a distal opening. The coil anchor can further include at least one coil retaining element configured to retain the embolic coil while permitting blood flow within the blood vessel. In particular, the coil anchor can be adapted to permit at least some blood flow within the blood vessel prior to the initiation of thrombosis and occlusion of the vessel.

In another embodiment described herein, embolic coils can be trapped at a location immediately adjacent to the implanted coil anchor. For example, the coil anchor can include an upstream end that is configured to prevent migration of embolic coils, while allowing at least some blood flow. In another aspect, each end of the coil anchor body includes a coil retaining element.

Further described herein are various methods for preventing embolic coil migration. In one embodiment, the methods can include positioning a coil anchor in a large diameter blood vessel, wherein the coil anchor includes a radially expandable sidewall, a proximal opening dimensioned to receive an embolic coil, and a distal opening dimensioned to permit blood flow within the blood vessel prior to thrombosis/occlusion. The coil anchor can also include at least one coil retaining element configured to retain the embolic coil within the blood vessel. The method can further include the steps of expanding the coil anchor within the blood vessel and delivering at least one embolic coil into the blood vessel, wherein the retaining element can prevent the at least one embolic coil from migrating downstream of the coil anchor.

The embolic coils can be delivered at a variety of locations relative to the coil anchor. For example, with the coil anchor positioned at a target vascular site, embolic coils can be delivered into the vasculature at a location upstream of the coil anchor. After moving into contact with the coil anchor, the embolic coils are prevented from further migration. In another embodiment, the embolic coils can be delivered into an interior portion of the coil anchor and/or can be delivered to a location immediately adjacent the coil anchor. In one such aspect, a portion of the coil anchor can be configured for mating with a coil delivery device, such as, for example, a catheter.

In another embodiment, an occlusion system is provided herein. The system can include an embolic coil and a coil anchor configured for placement within a large diameter blood vessel, wherein the coil anchor includes a radially expandable sidewall, a proximal opening dimensioned to receive the embolic coil, and a distal opening. The coil anchor further includes at least one coil retaining element configured to retain the embolic coil within the blood vessel.

Additional aspects and advantages of the invention will be set forth in part in the description which follows, and in part will be apparent from the description, or can be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Described herein are various methods and systems for preventing unwanted migration of an implantable occlusive device, particularly, embolic coils. One such system includes a coil anchor adapted for implantation within a vascular structure, such as, for example, a blood vessel. The coil anchor can be positioned within a large diameter blood vessel at a target location and expanded to mate with the blood vessel. A lumen of the implanted coil anchor can receive and trap one or more embolic coils introduced to the coil anchor. These trapped coils can function to occlude the blood vessel at the desired location, and the coil anchor can minimize the risk of coil migration. In some embodiments the coil anchor can be configured for permanent or long-term placement within the blood vessel.

Figure 1:
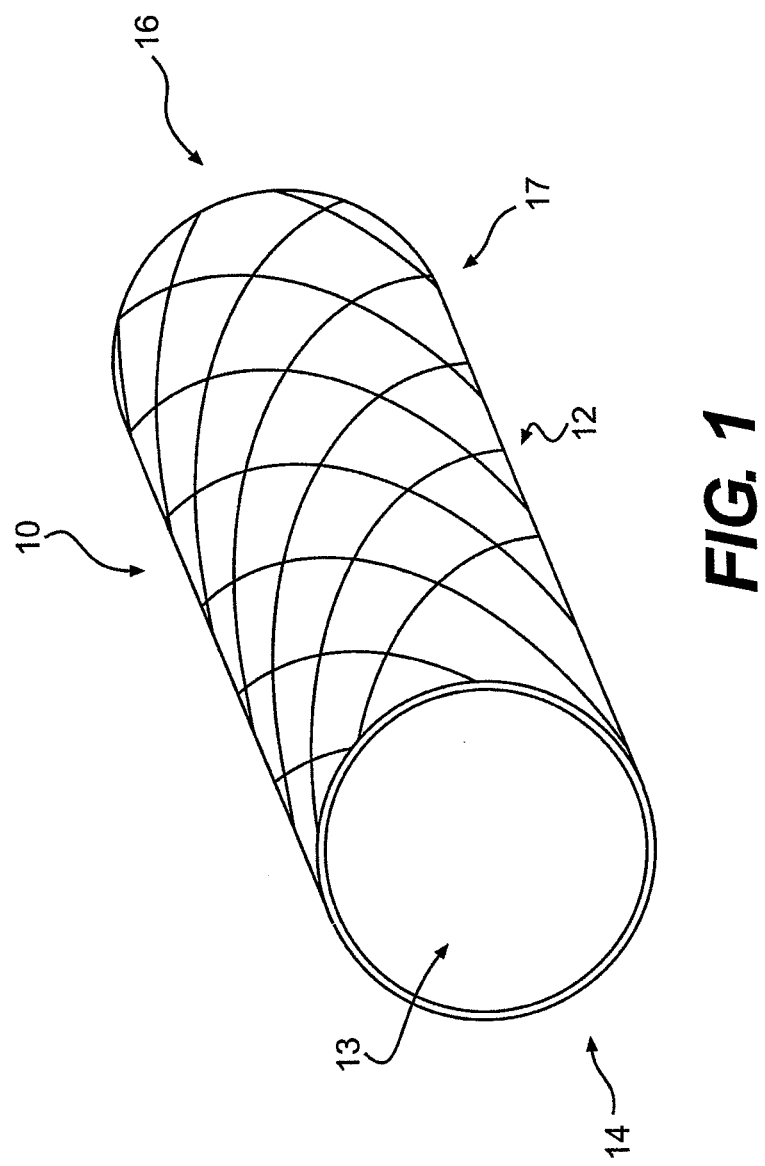
FIG. 1 illustrates a perspective view of a coil anchor, according to an exemplary disclosed embodiment.

FIG. 1 illustrates a perspective view of a coil anchor 10, according to an exemplary embodiment. Coil anchor 10 includes an anchor body 12, wherein anchor body 12 includes a lumen 13 extending from a proximal opening 14 to a distal opening 16 of anchor body 12. Coil anchor 10 can be positioned in a blood vessel (not shown) such that blood flow can enter proximal opening 14, flow through lumen 13, and exit coil anchor 10 via distal opening 16. Proximal opening 14 can also be dimensioned and configured to receive one or more embolic coils (not shown). Coil anchor 10 can also include features adapted to trap coils within lumen 13 and prevent coil migration, as described below. For example, a coil retaining element (not shown) can be positioned within lumen 13, at proximal opening 14, and/or at distal opening 16 of coil anchor 10.

Anchor body 12 can assume a variety of shapes and sizes for placement within a blood vessel, such as, for example, a vessel having an inner diameter in the range of about 2 mm and 30 mm. For example, anchor body 12 can include an outer shape that generally corresponds, at least in part, to an anatomical feature of a blood vessel, such as, a generally cylindrical structure. A variety of alternative elongate anchor body shapes are also contemplated, including, for example, elongate shapes having a varying width.

Regardless of the coil anchor shape, in one aspect, anchor body 12 has an outer dimension approximately equal to or greater than an inner diameter of a blood vessel. In another aspect, anchor body 12 can have a diameter smaller than the diameter of a target blood vessel and can expand to meet or exceed the inner diameter of the blood vessel. The force of the anchor body against the blood vessel walls can maintain the coil anchor at a target site. For example, anchor body 12 can be configured to expand to a dimension of at least about 10%, 20%, 50%, or 100% beyond the inner diameter of a target blood vessel. The amount of expansion can be varied, for example, depending on the desired implantation site, local blood vessel integrity, and/or intended use of the coil anchor system. For example, expansion, in one aspect, can permanently implant coil anchor 10 within a blood vessel.

Anchor body 12 can include a sidewall 17 formed from a variety of biocompatible materials, such as, for example, a metal alloy or a polymer. Such materials include stainless steel, titanium, nickel alloys, platinum, and combinations thereof.

Polymer materials can include polyethyleneterepthalate (PET), polyetheretherketone (PEEK), polysulfone, polytetrafluoroethylene (PTFE), expanded polytetrafluoroethylene (ePTFE), fluorinated ethylene propylene (FEP), polycarbonate urethane, polypropylene, polyethylene, high density polyethylene (HDPE), silicone, polyurethane, and combinations thereof. Also, anchor body 12 could form a hybrid structure composed of multiple materials, types, and/or conformations. In one such embodiment, anchor body 12 can include a polymer coating (not shown), wherein the polymer coating extends between structural members of sidewall 17 such that a partial barrier exists between an outer surface of anchor body 12 and an inner surface of anchor body 12. In other embodiments, a polymer coating can encase structural members of sidewall 17 to limit exposure of the structural members to a physiological environment within the blood vessel.

In one aspect, the materials forming sidewall 17 are radially expandable. In particular, anchor body 12 can be self-expanding, whereby sidewall 17 expands upon removal of a constraining force. For example, a radial expansion of anchor body 12 could be constrained by a sheath (not shown), or similar structure, at least partially covering sidewall 17. Sidewall 17 can also include a super-elastic material, such as a nickel-titanium alloy, or other material with shape-memory properties capable of expansion upon changes in temperature. For example, sidewall 17 can expand from a collapsed configuration to an expanded configuration when heated to a body temperature. In another aspect, the expandable anchor body 12 is not self-expanding and an insertion device, such as a balloon catheter (not shown), can be used to expand sidewall 17 to form an expanded anchor body 12.

In one embodiment, proximal opening 14 can extend across the full width of anchor body 12. Alternatively, coil anchor 10 can include multiple proximal openings (not illustrated), at least some of which are sized for receiving embolic coils. Where the coil anchor is configured to receive embolic coils within lumen 13, the proximal (or upstream) end of the anchor body can be configured to mate with an embolic coil delivery device (i.e., the distal end of a catheter). For example, proximal opening 14 can have a size and shape corresponding to a distal opening of a delivery catheter. In addition, or alternatively, the anchor body can have a tapered region to facilitate mating and/or to direct the outer surface of a delivery catheter into the inner lumen of coil anchor 10.

Further, anchor body 12 can be bifurcated wherein the structure may be branched (not shown). Specifically, a bifurcated structure can include two or more distal openings such that the bifurcated structure could be placed within a bifurcated blood vessel. The bifurcated blood vessel could provide a resistive force to counteract forces caused by blood flow. In another embodiment, anchor body 12 can include proximal opening 14, having a first dimension, and distal opening 16, having a second, smaller dimension. The first and second dimensions can be measured as a diameter, a circumference, a cross-sectional width, and/or a cross-sectional area. In addition, the proximal and distal openings can have a variety of shapes, such as, for example, a circular, elliptical, and irregular shape.

Figure 2:
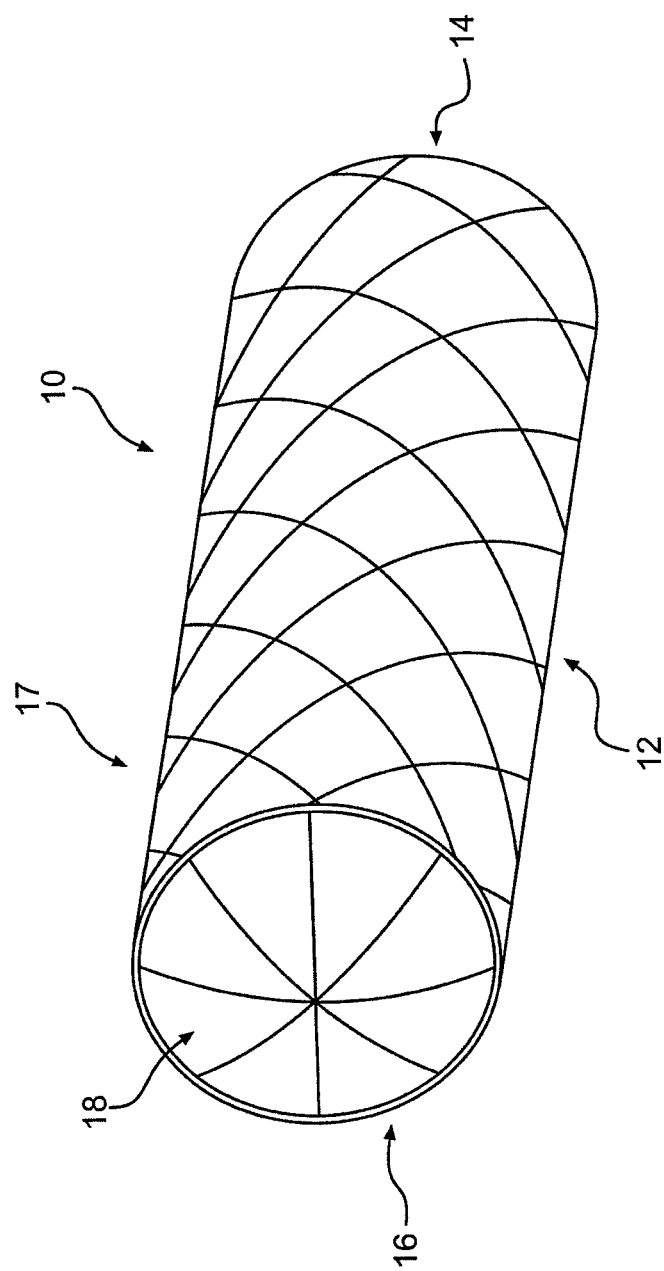
FIG. 2 illustrates another perspective view of a coil anchor, according to an exemplary disclosed embodiment.

FIG. 2 illustrates a distal perspective view of coil anchor 10 showing a retaining element 18 located at distal opening 16. In one embodiment, retaining element 18 and sidewall 17 have a unitary construction, wherein the distal portion of sidewall 17 defines retaining element 18. In another embodiment, retaining element 18 can be defined by a separate element mated with sidewall 17. Irrespective of the configuration of retaining element 18, sidewall 17 and retaining element 18 are configured to trap or retain an embolic coil while permitting at least some blood flow through lumen 13. In particular, prior to the initiating thrombosis and the formation of an occlusion, the coil anchor can be configured to allow at least some blood flow.

Retaining element 18 could have a variety of shapes configured for positioning within lumen 13. In one aspect, the cross-sectional shape of retaining element 18 could correspond to the inner surface of lumen 13. Alternatively, retaining element 18 could have a shape different from an inner circumference of anchor body 12. Such an arrangement of elements could permit blood flow through regions formed between the outer perimeter of retaining element 13 and the inner wall of lumen 13.

In one aspect, retaining element 18 can include one or more apertures sized to permit blood flow but small enough to prevent the passage of an embolic coil. One skilled in the art will appreciate that the size and number of apertures can be chosen based on the blood vessel targeted for occlusion, the desired blood flow, and/or the dimensions of the embolic coils used with coil anchor 10.

Figure 3A:
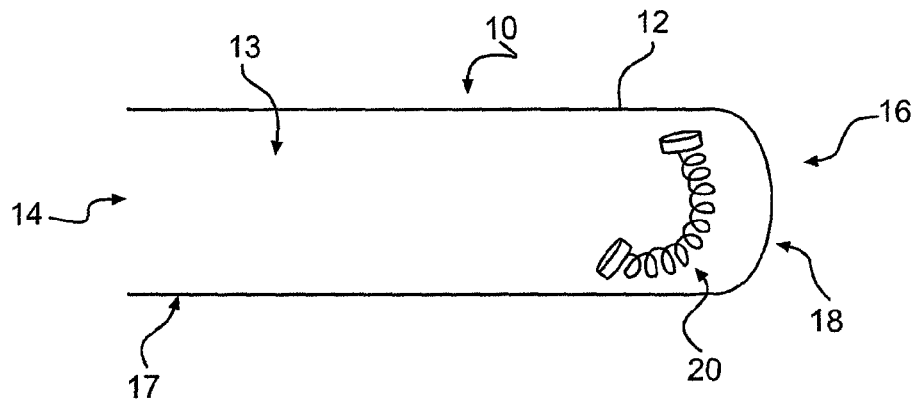
FIG. 3A illustrates a longitudinal cross-sectional view of a coil anchor, according to an exemplary disclosed embodiment.

As mentioned above, retaining element 18 is adapted to trap embolic coils within lumen 13. FIG. 3A illustrates a longitudinal cross-sectional view of coil anchor 10, with an embolic coil 20 trapped by distally positioned retaining element 18. In one embodiment, lumen 13 is sized and shaped to receive multiple coils.

Embolic coils 20 are often made of wire having a diameter ranging from 0.0254 mm to 1.3 mm, and the resulting coil diameter is typically in the range of 0.1 to 2.2 mm. One skilled in the art will appreciate that the coil diameter can vary depending on the intended use, such as, for example, vessel size. Commensurate with coil dimensions, retaining element 18 can define a series of apertures sized to trap coils while permitting blood flow. In one embodiment, retaining element 18 has a maximum aperture width of less than about 3 mm. In other embodiments, retaining element 18 has a maximum aperture width in the range of about 3 mm and 0.01 mm, preferably 2.5 mm and 0.1 mm, and more preferably 2.0 and 0.1 mm.

Figure 3B:
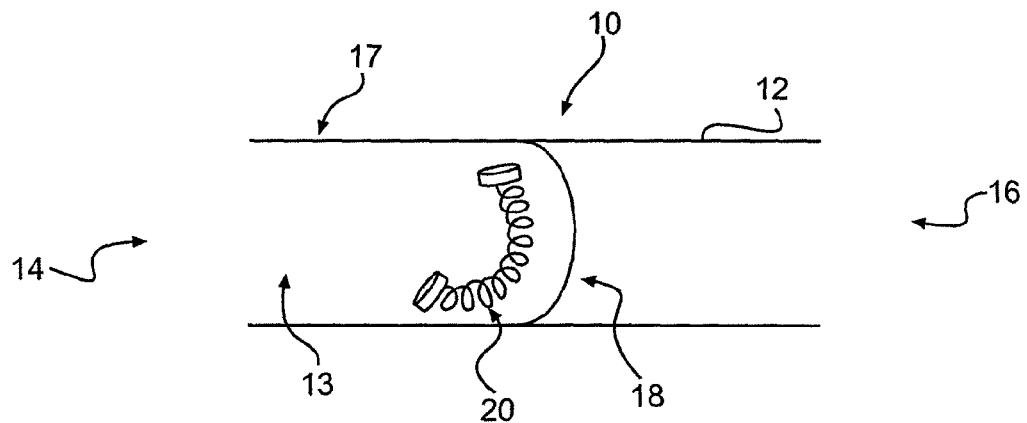
FIG. 3B illustrates a longitudinal cross-sectional view of a coil anchor, according to another exemplary disclosed embodiment.

Retaining element 18 can be positioned at a variety of locations within lumen 13 to prevent the migration of embolic coils beyond coil anchor 10. FIG. 3B illustrates a longitudinal cross-sectional view of coil anchor 10, according to another exemplary disclosed embodiment wherein retaining element 18 is positioned between proximal opening 14 and distal opening 16.

In another embodiment, the retaining element can be positioned proximate to the proximal end the anchor body. Embolic coils delivered upstream of the coil anchor are then trapped adjacent to the anchor body, instead of within the anchor body (not illustrated). In still another embodiment, multiple retaining elements are placed along the length of the anchor body. For example, retaining elements can be located proximate to both the proximal and distal ends of the anchor body. In such a configuration, the direction of implantation does not affect coil location. Regardless of which end of the coil anchor is inserted first, embolic coils will collect at a site adjacent to the upstream end of the coil anchor.

As mentioned above, retaining element 18 can assume a variety of structures. In one embodiment, retaining element 18 includes a body extending in a non-parallel direction with respect to the elongate anchor body 12. For example, the retaining element can extend in a direction generally transverse to the anchor body.

In another embodiment, retaining element 18 is defined by multiple bodies at least partially extending across lumen 13. For example, as shown in FIG. 2, retaining element 18 can include a plurality of wires extending from approximately opposite locations on the perimeter of sidewall 17 at distal opening 16.

Figure 4A:
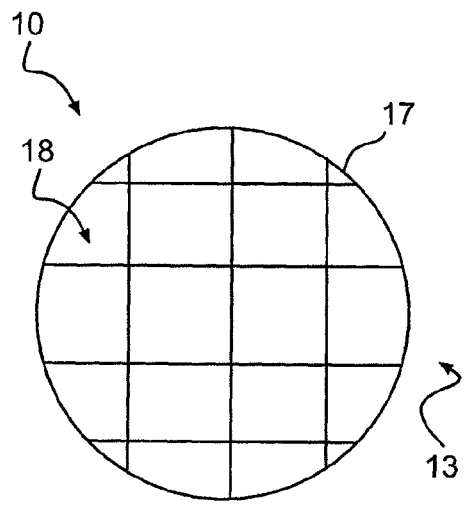
FIG. 4A illustrates a lateral cross-sectional view of a coil anchor, according to an exemplary disclosed embodiment.
Figure 4B:
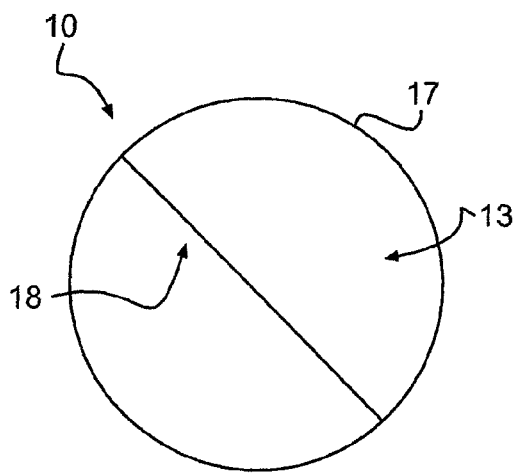
FIG. 4B illustrates a lateral cross-sectional view of a coil anchor, according to an exemplary disclosed embodiment.

For example, as shown in FIG. 4A, retaining element 18 can include a net formed by a series of perpendicular wires extending across a portion of lumen 13. Such a net structure could permit blood flow through lumen 13 when no coil is present, yet trap a coil within lumen 13 as the open regions defined by net the are smaller than an outer dimension of a coil. In some embodiments, a single wire may be sufficient to form retaining element 18, as shown in FIG. 4B, illustrating a lateral plane of coil anchor 10.

Figure 4C:
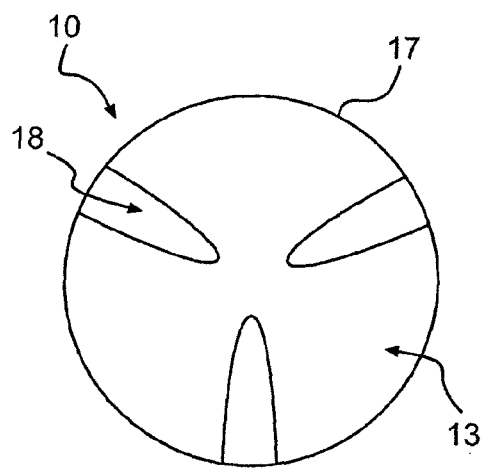
FIG. 4C illustrates a lateral cross-sectional view of a coil anchor, according to an exemplary disclosed embodiment.

In another aspect, retaining element 18 can be formed by a structure that extends across only a portion of lumen 13. For example, hooks, threads, knobs, and/or spikes can extend from the inner surface of sidewall 17 into lumen 13 to trap coils, as shown in FIG. 4C, illustrating a lateral plane of coil anchor 10 showing retaining element 18 with three knobs. In one aspect, retaining elements 18 positioned within lumen 13 can be formed integrally with sidewall 17. Alternatively, or additionally, retaining elements 18 can be mated with the inner wall of anchor body 12. One skilled in the art will appreciate that retaining elements 18 can be mated with sidewall 17 and/or each other in a variety of ways, such as, for example, tied, adhered, welded, and/or hingedly attached.

Figure 5A:
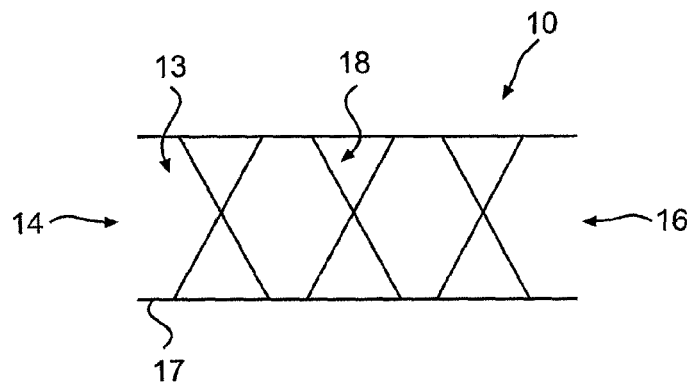
FIG. 5A illustrates a longitudinal cross-sectional view of a coil anchor, according to an exemplary disclosed embodiment.
Figure 5B:
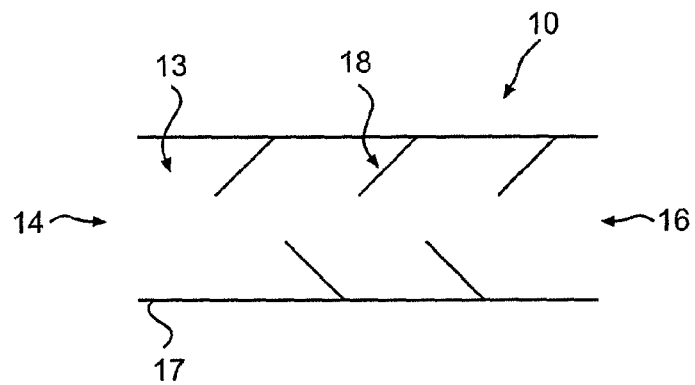
FIG. 5B illustrates a longitudinal cross-sectional view of a coil anchor, according to a further exemplary disclosed embodiment.

FIG. 5A illustrates a longitudinal cross-sectional view of coil anchor 10, wherein retaining element 18 can extend in an at least partially longitudinal direction with respect to elongate anchor body 12. As shown in FIG. 5A, retaining element 18 can include one or more wires mated with longitudinally spaced portions of lumen 13. Further, retaining element 18 can include components positioned at an angle such that one portion of retaining element 18 is positioned proximally with respect to another portion of retaining element 18. FIG. 5B illustrates retaining element 18 including hooks, barbs, and/or spikes extending in a distal to proximal direction to facilitate trapping coils.

Figure 5C:
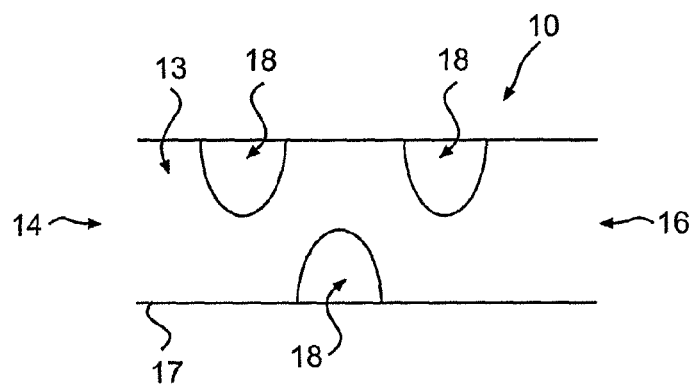
FIG. 5C illustrates a longitudinal cross-sectional view of a coil anchor, according to another exemplary disclosed embodiment.

In some embodiments, coil anchor 10 can include multiple retaining elements 18, as shown in FIG. 5C. Such retaining elements 18 can provide a tortuous flow path for one or more embolic coils placed upstream, or into, coil anchor 10. Upstream retaining elements can be spaced to allow coil movement while downstream retaining elements prevent coils from slipping by and exiting lumen 13.

Retaining element 18 can further have a longitudinal thickness that extends along a portion of lumen 13. In one aspect, one or more retaining elements 18 can extend the full length of anchor body 10 or lumen 13. Alternatively, one or more retaining elements 18 can extend across at least 50 percent of the length of anchor body 10 or lumen 13. Alternatively, retaining element 18 can extend across about 1 to 50 percent, about 5 to 25 percent, or about 5 to 15 percent of anchor body 10 or lumen 13.

In one aspect, retaining element 18 can include similar structural properties of sidewall 17, as described elsewhere. For example, retaining element 18 can be formed of self expanding mesh that expands and contracts with sidewall 17 to facilitate insertion of anchor body 12 into a blood vessel. Retaining element 18 can also include an elastic material at least partially covering a cross-section of anchor body 12 and/or lumen 13. In addition, retaining element 18 can include any material, structure, or other physical property as described elsewhere for anchor body 12, such as, for example, a wire frame or a shape-memory alloy.

Retaining element 18 can be expandable such that expansion of anchor body 12 can also expand retaining element 18. For example, retaining element 18 can be hingedly and/or slideably attached to anchor body 12 such that expansion of anchor body 12 results in a movement of retaining element 18 relative to anchor body 12. Such relative movement can permit retention element 18 to assume one configuration when coil anchor 10 is collapsed and another configuration when coil anchor 10 is expanded.

Also, retaining element 18 can be configured to permit placement of a guidewire through and beyond coil anchor 10. For example, retaining element 18 can include a central lumen (not shown) dimensioned to accommodate a guidewire, while preventing the transit of an embolic coil. The central lumen can have a diameter larger than a standard guidewire, wherein the lumen permits coil anchor 10 to slide over the standard guidewire during positioning or deployment of coil anchor 10.

Figure 6:
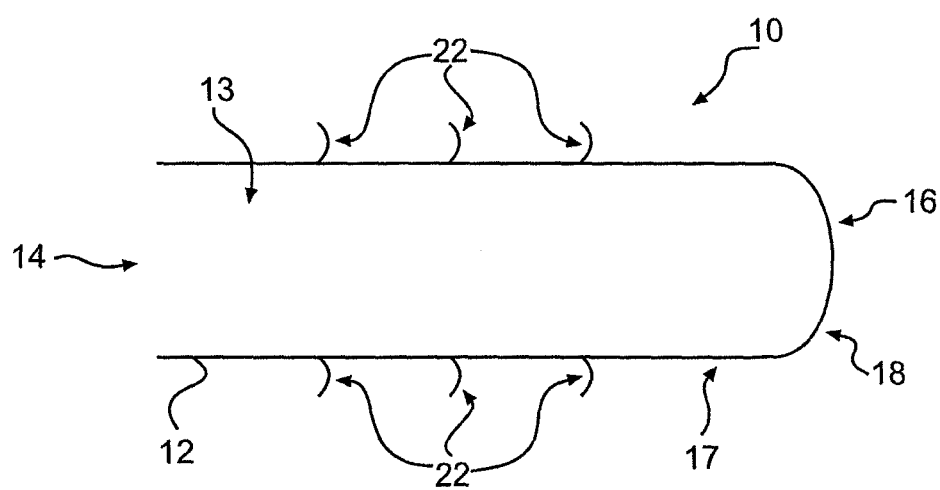
FIG. 6 illustrates a longitudinal cross-sectional view of a coil anchor, according to an exemplary disclosed embodiment.

FIG. 6 illustrates a cross-sectional view of coil anchor 10, according to an exemplary disclosed embodiment wherein anchor body 12 can include one or more surface features 22. The one or more surface features 22 can include a structure configured to assist retention of coil anchor 10 within a blood vessel (not shown). For example, surface feature 22 can include a knob, a hook, a barb, or any other structure configured to at least partially maintain a position of expanded coil anchor 10 at a desired location within a blood vessel. Surface features 22 can further be configured to permanently anchor coil anchor 10 within a high-flow blood vessel.

In another embodiment described herein, coil anchor 10 can include one or more therapeutic materials. For example, substances may also be added to mitigate inflammation, suppress an immune response, or for any other suitable process. Such materials can include fibers, polymers, gels, compounds, biological molecules, or any other materials known in the art. For example, coil anchor 10 can include thrombosis-promoting materials that enhance the occlusion process. Such thrombotic materials can trap blood cells, provide a structure for cell adhesion, activate at least part of a coagulation cascade, and/or stimulate a process associated with thrombosis. In one aspect, anchor body 12 includes thrombosis promoting fibers having a fabric or gauze-like structure, and/or positioned in a non-woven or loose agglomeration of individual fibers. The fibers can be mated with sidewall 17 such that the fibers extend into lumen 13 to promote thrombosis formation in combination with a coil within the interior of and/or around anchor body 12. In addition, fibers can be positioned on an outer surface of the coil anchor to promote thrombosis and to facilitate mating of anchor body 12 with a blood vessel. The fibers can also extend from and/or be received within retaining element 18. The fibers can be formed from polymer materials, such as, for example polyethylene, polyacrylics, polypropylene, polyvinylchloride, polyamides such as nylon, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and combinations thereof.

Coil anchor 10 can be implanted within a blood vessel using any suitable medical technique. For example, coil anchor 10 can be positioned within a blood vessel using a catheter or similar percutaneous device. Before implantation, coil anchor 10 can be collapsed on a distal region of a catheter such that coil anchor 10 may assume an outer diameter suitable for placement within a blood vessel. The catheter containing collapsed coil anchor 10 may then be positioned within a blood vessel using any suitable medical imaging (i.e. radiological) technique, such as fluoroscopy.

In some embodiments, coil anchor 10 can include one or more markers (not shown) configured to permit positioning within a blood vessel using any suitable positioning technique. For example, coil anchor 10 can include one or more radio-opaque markers, configured to permit positioning of coil anchor 10 using fluoroscopy. Such a marker could also assist subsequent positioning and placement of embolic coils in coil anchor 10. In particular, delivery catheters and/or embolic coils incorporating radio-opaque markers could be aligned or positioned relative to similar markers on coil anchor 10. Using markers on coil anchor 10 for subsequent coil delivery can permit safe occlusion of sites that could be difficult to treat using traditional occlusion devices and delivery techniques.

After positioning coil anchor 10 at a desired site within a blood vessel, coil anchor 10 can be expanded. For example, coil anchor 10 can be expanded using a balloon catheter, wherein a balloon may inflate to expand coil anchor 10. Coil anchor 10 can also be self-expanding, whereby a delivery catheter may include a retractable sheath configured to release coil anchor 10 from a collapsed state. When the sheath retracts, the coil anchor can assume an expanded configuration. It is also contemplated that coil anchor 10 can be constructed of a shape-memory alloy capable of expanding upon temperature activation.

Expansion of coil anchor 10 within the blood vessel should sufficiently mate coil anchor 10 with the vessel such that coil anchor 10 is maintained at a target site of occlusion. Coil anchor 10 must be expanded such that the mating of coil anchor 10 and the vessel can provide enough resistive force to counteract forces applied to a partially or fully occluded coil anchor 10. The forces applied to coil anchor 10 following coil deployment are due to upstream blood pressure developed following partial or complete vessel occlusion. Coil anchor 10 should be expanded such that pressure between coil anchor 10 and the blood vessel are sufficient to maintain a position of coil anchor 10. Alternatively, as mentioned above, the outer surface of coil anchor 10 can include surface features 22 that provide additional resistive forces against movement of coil anchor 10, such as hooks to grip the vessel. In yet another embodiment, the shape of the vessel can help to prevent movement of coil anchor 10. For example, sidewall 17 of coil anchor 10 can conform to a recess or protrusion within a vascular channel.

Following expansion and placement of coil anchor 10, a delivery catheter may be withdrawn. One of more embolic coils can then be placed within coil anchor 10 using any suitable technique. For example, embolic coils could be placed upstream of coil anchor 10 such that the coils could flow into proximal opening 14 and be retained by retaining element 18. Alternatively, an embolic coil can be placed directly within coil anchor 10 and upstream of retaining element 18 such that blood flow and/or blood pressure may force the embolic coil against retaining element 18. Either technique can be used to place one or more embolic coils within coil anchor 10 to cause partial or complete blood vessel occlusion.

Coil placement within coil anchor 10 can be performed immediately following placement of coil anchor 10 within a blood vessel, or at some later time. Such a multi-stage occlusion process could be beneficial for various reasons, such as, for example, to confirm a location of coil anchor 10 within a vessel before partially or fully occluding the vessel. Further, another imaging technique could be used to confirm appropriate placement of coil anchor 10, to determine a relative position between coil anchor 10 and a lesion to be treated, or to monitor blood flow within the vessel targeted for occlusion following placement of coil anchor 10.

The multi-stage occlusion process could also include sequential coil deployment, whereby one embolic coil at a time is added to a suitably positioned coil anchor 10. Such a process can permit gradual vessel occlusion as each coil can be added and blood flow monitored to determine any reduction in blood flow. Retraction and/or repositioning of one or more coils, or coil anchor 10 may permit precise occlusion of large diameter vessels that would normally be difficult using existing devices and surgical methods.

Preferred embodiments of the present invention have been described above. Those skilled in the art will understand, however, that changes and modifications may be made to these embodiments without departing from the true scope and spirit of the invention, which is defined by the claims.

The invention claimed is:

1. A vessel occlusion method, the method comprising the steps, in the order recited, of
positioning a coil anchor in a large diameter blood vessel, wherein the coil anchor includes a radially expandable sidewall, a proximal opening dimensioned to receive an embolic coil, a distal opening, and the coil anchor further comprising at least one coil retaining element located within a lumen of the coil anchor configured to retain an embolic coil within the blood vessel;
expanding the coil anchor within the blood vessel; and
delivering at least one embolic coil into the blood vessel, wherein the retaining element prevents the at least one embolic coil from migrating downstream of the coil anchor.

2. The method of claim 1, wherein the coil anchor is generally cylindrical.

3. The method of claim 2, wherein the coil anchor has an outer diameter in a range of about 2 mm to 30 mm.

4. The method of claim 1, wherein the retaining element is positioned at the distal opening.

5. The method of claim 4, wherein a second retaining element is positioned proximate to the proximal opening.

6. The method of claim 1, wherein the retaining element is positioned between the proximal opening and the distal opening.

7. The method of claim 1, wherein the retaining element includes at least one of multiple wires extending across an inner region of the anchor body, a net, an internal protrusion extending from an inner wall of the anchor body, and combinations thereof.

8. The method of claim 7, wherein the internal protrusion includes at east one of a knob, a hook, a barb, a threaded structure and combinations thereof.

9. The method of claim 1, wherein the coil anchor further includes one or more materials configured to promote thrombosis.

* * * * *